United States Patent [19]

Reinhard

[11] Patent Number: 5,139,333
[45] Date of Patent: Aug. 18, 1992

[54] MEASURING CELL FOR THE SPECTRAL ANALYSIS OF FLOWING MEDIA, IN PARTICULAR PLASTIC MELTS

[75] Inventor: Michael Reinhard, Schaafheim, Fed. Rep. of Germany

[73] Assignee: Automatik Apparate-Maschinebau GmbH, Grossostheim, Fed. Rep. of Germany

[21] Appl. No.: 679,055
[22] PCT Filed: Nov. 8, 1989
[86] PCT No.: PCT/DE89/00704
 § 371 Date: Jul. 10, 1991
 § 102(e) Date: Jul. 10, 1991
[87] PCT Pub. No.: WO90/05292
 PCT Pub. Date: May 17, 1990

[30] Foreign Application Priority Data

Nov. 11, 1988 [DE] Fed. Rep. of Germany ....... 3838371

[51] Int. Cl.$^5$ ............................................. G01N 21/05
[52] U.S. Cl. ....................................... 356/246; 356/440
[58] Field of Search ................ 356/246, 440; 250/576

[56] References Cited

U.S. PATENT DOCUMENTS 3,740,156 6/1973 Heigl et al. .................... 356/246 X
3,810,695 5/1974 Shea ............................... 356/246 X

FOREIGN PATENT DOCUMENTS 817547 3/1971 U.S.S.R. .

OTHER PUBLICATIONS

Smith et al "Infra-red Absorption Cells and Measurement of Cell Thickness", Josa, vol. 34 #3, Mar. 1944, pp. 130–134.
Stromberg et al "A Window-Configuration for High Pressure Optical Cells" Rev. of Scientific Instruments, vol. 41 #12, pp. 1880–1881.

Primary Examiner—Vincent P. McGraw
Attorney, Agent, or Firm—Banner, Birch, McKie & Beckett

[57] ABSTRACT

Measuring cell for the spectral analysis of flowing media, in particular plastic melts, in which cell the medium to be analyzed flows between two opposing windows made of a radiation transparent material and is penetrated by radiation, where at least one window is held in a pipe, which can be moved by axial motion in the direction of the second window or away from said window in a bore of the measuring cell body with said measuring cell body being sealed, where the width of the gap between the windows and thus the layer thickness of the medium through which the radiation is to travel is variable. The pipe abuts in the region of the seal with a stepless cylindrical outer surface directly against the wall of the bore and in this region exhibits oversize in the disassembled state relative to the bore. The wall thickness of the pipe is small with respect to the outer diameter of the pipe at least in the region of the seal. A layer of adhesive is inserted in a ring slot between the interior of the pipe and the shell of the window.

8 Claims, 1 Drawing Sheet

MEASURING CELL FOR THE SPECTRAL ANALYSIS OF FLOWING MEDIA, IN PARTICULAR PLASTIC MELTS

The invention relates to a measuring cell for the spectral analysis of flowing media, in particular plastic melts, in which cell the medium to be analyzed flows between two opposing windows made of a radiation transparent material and is penetrated by radiation, where at least one window is held in a pipe, which can be moved by axial motion in the direction of the second window or away from said window in a bore of the measuring cell body with said measuring cell body being sealed, where the width of the gap between the windows and thus the layer thickness of the medium through which the radiation is to travel is variable.

The construction of such a measuring cell follows from the U.S. Pat. No. 3,177,706. In this measuring cell two windows, between whose opposing window faces the medium flows by, can be moved towards one another and away from one another. This occurs here by turning the respective receptacle for the windows, which are designed as pipes, offset stepwise, and are screwed with an external thread into the internal thread in the bore of the measuring cell body. Into one of the steps in the region between the thread and the face of the pipe is inserted a sealing ring that is made of an elastic material and that provides that no melt material that has penetrated between the inner wall of the bore of the measuring cell body and the outer surface of the pipe can escape beyond the sealing ring into the thread and to the outside.

Since the measuring cells must withstand a pressure of the flowing medium in a magnitude of several 100 bar, and in particular at temperatures of up to some 100° C., extreme requirements are placed on the seal between the pipe and the measuring cell body.

Therefore, the invention is based on the problem of designing the measuring cell body and pipe in such a manner that with simple construction high pressures, in particular at high temperatures, a seal can be achieved without any problems. According to the invention, such a seal is obtained in that the cylindrical outer diameter of the pipe abuts in the region of the seal with the stepless cylindrical diameter directly against the wall of the bore and in this region exhibits oversize in the disassembled state relative to the bore, in that the wall thickness of the pipe is small with respect to the outer diameter of the pipe at least in the region of the seal and in that a layer of adhesive is inserted in a ring slot between the interior of the pipe and the shell of the window.

With this design the object is to obtain a high sealing surface compression through the direct abutting of the stepless cylindrical outer surface of the pipe against the wall of the bore without the axial mobility of the pipe in the bore of the measuring cell body being too severely hindered. This goes back to the fact that due to the relatively negligible wall thickness of the pipe, said pipe can be negligibly compressed owing to the elasticity bestowed on said pipe due to said relatively negligible wall thickness so that the sealing surface compression cannot increase excessively. The pipe enables in a simple manner the seal with respect to the window, which with its shell forms relative to the interior of the pipe a ring slot into which a layer of adhesive is inserted.

The region of the seal is designed in such a manner advantageously that said seal extends as far as the end of the bore of the measuring cell body that faces the medium. Thus it is avoided that at the face of the pipe the medium can enter between the outer surface of the pipe and the wall of the bore, so that thus the foremost point of the pipe is sealed, thus ruling out dead spaces in which the medium could collect.

To protect the window from too high radial stresses, a material that is elastic compared to the material of the window and the pipe is used. Thus, it is achieved that the elastic compression of the pipe is absorbed by the elastic material of the adhesive layer and is thus not transferred to the window. This is especially important if due to reasons relating to the respective spectral analysis a material has to be used for the window that exhibits high brittleness.

The seal between the interior of the pipe and the shell of the window can be designed as a cone, to which end the shell of the window extends in the direction of the medium conically with the increase in diameter and the pipe exhibits a corresponding internal cone. When the window is pressed into the inner cone coated with a layer of adhesive, a thin layer of adhesive, which produces the seal, results automatically depending on the strength of the insertion.

In order to be able to adjust, on the one hand, especially weak layer thicknesses for the medium between the opposing windows and to avoid, on the other hand, with certainty that when moving the windows towards one another they meet, the connection of pipe and window is designed in such a manner that the window surface facing the medium does not project in front of the face of the pipe and lies substantially in one plane with this face. In this design very thin layers can be adjusted for the medium between the window surfaces, where, however, it remains guaranteed that the window surfaces cannot meet, since in this moving towards one another the faces of the pipes would finally clash. This is of special importance because a collision of window surfaces could destroy the windows.

To also enable more frequent adjustment of the layer thickness of the medium, the outer surface of the pipe is logically made of wear resistant material at least in the region of the pipe's seal. The same also applies to the inner wall of the bore. Constructively this can be accomplished in that wear resistant material is applied subsequently either on the surface or wall in question or in that the components in question are made of a wear resistant material.

To avoid that the pipe rotate during its axial displacement in the bore of the measuring cell, the pipe can be provided with an anti-rotation element in a region facing away from the window. This is meaningful especially when the pipe is provided in known manner on its side facing away from the window with a thread in which an internal thread engages.

Twisting the affected nut to be secured axially produces then a corresponding axial displacement of the pipe and thus a corresponding adjustment of the layer thickness.

The figures show embodiments of the invention.

Figure 1:
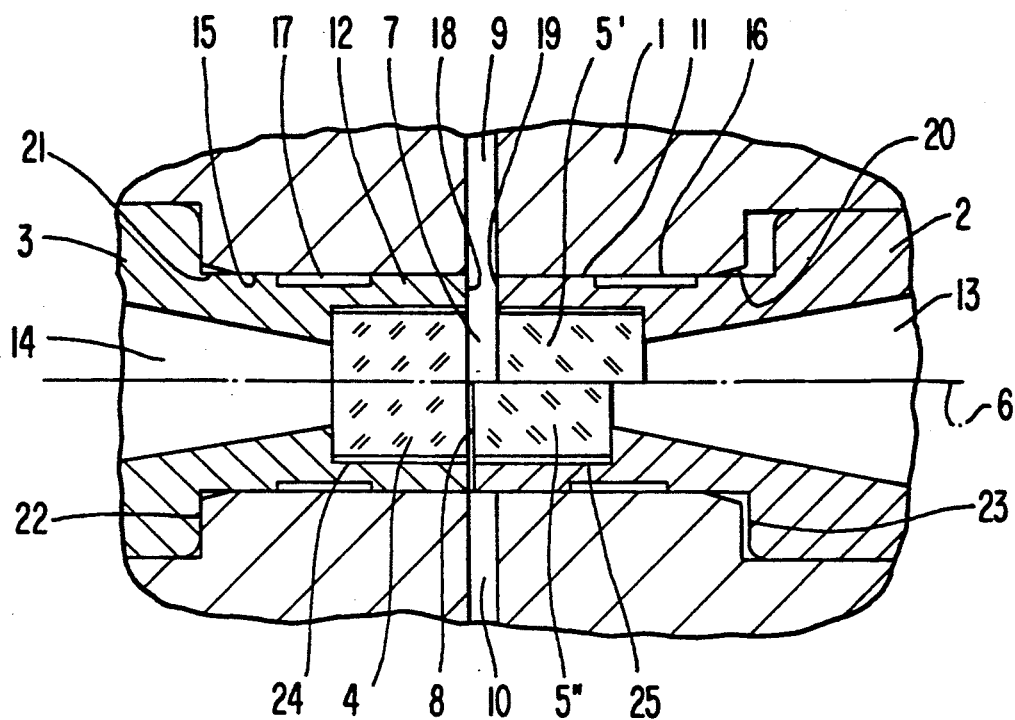
FIG. 1 is a cross sectional view of a measuring cell with windows that exhibit a cylindrical shell.

FIG. 1 is a cross sectional view of the measuring cell, which comprises the measuring cell body 1 and the two pipes 2 and 3, which bear the windows 4 and 5 on the sides facing one another. The window 5 is drawn in two positions by means of an imaginery cross section along the center line 6. In the position of window 5 denoted as 5', said window observes the distance forming gap 7 from window 4, whereas in position 5" drawn below the center line, the window 5 leaves free an especially narrow gap 8. The two positions of the window 5 (5' or 5") that are shown clarify the variable width of gap 7 or 8 between the windows 4 and 5.

The flowing medium is fed to the gap 7 or 8 by means of the passages 9 and 10 in the measuring cell body 1, which opens into gap 7 or 8.

Pipes 2 and 3 form in the region of windows 4 and 5 relatively thin-walled hollow cylinders 11 and 12, whose thickness is so small that the hollow cylinders 11 and 12 exhibit a specific elasticity. Owing to the oversize of the pipes 2 and 3 that appears in the disassembled state with respect to the bore 15 receiving pipes 2 and 3, the two hollow cylinders 11 and 12 can be thus negligibly flexible radially towards the inside, thus resulting in a desired high sealing surface compression between the outer diameter of pipes 2 and 3 and the inner diameter of bore 15. Owing to the elasticity of the two hollow cylinders 11 and 12, they maintain their axial mobility in bore 15 so that both pipe 2 and pipe 3 can be displaced axially without impairing the seal between pipe 2 or 3 and the measuring cell body 1.

To keep within bounds the friction, producted during the axial movement of pipes 2 and 3, between pipes 2 and 3 and the wall of bore 15, an annular recess 16 and 17 is machined into the outer surface of pipes 2 and 3, thus restricting the region of the seal between pipe 2 or 3 and bore 15 to the length between recess 16 or 17 and the affected face 18 or 19 of pipe 2 or 3, provided the face does not project above the edge of passage 9 or 10, as is the case with window 5 in its position 5" shown below the center line 6. In a position of window 4 or 5 in which said window projects into the region of passage 9 or 10, the region of the seal is thus shortened by the length of this inward projection. The two recesses 16 and 17 can be filled with a lubricant in order to prevent the parts that are adjacent and moved against one another from eroding each other.

The measuring cell body 1 is provided with insertion inclines 20 and 21 at the insertion points for pipes 2 and 3. The region of pipes 2 and 3 between recesses 16 and 17 and shoulders 22 and 23 do not exhibit an oversize; said region serves here only for guiding.

The two windows 4 and 5 are attached in pipes 2 and 3 by means of the layer of adhesive 24 and 25. For the adhesive layer is used here an elastic material that guarantees that when compressing hollow cylinders 11 and 12 too high a pressure is not transferred to windows 4 and 5.

Faces 18 and 19 of pipes 2 and 3 lie here in a plane with the surface of window 4 or 5 that faces gap 7 or 8. Thus, it is avoided that in the region of faces 18 and 19 are formed dead spaces in which medium flowing through gap 7 or 8 can settle. If it is to be provided that when moving windows 4 and 5 together their surfaces facing one another are not supposed to touch, the faces 18 and 19 project slightly with respect to the affected surfaces of windows 4 and 5.

The two pipes 3 and 4 with windows 4 and 5 can be moved axially in known manner by means of a thread that is cut on the side of pipes 2 and 3 that faces away from windows 4 and 5 and with which an internal thread of an axially secured, rotatable nut engages. In order now for pipe 2 or 3 not to turn when the nut that is not shown here is rotated, each pipe 2 or 3 is provided with an anti-rotation element, which is formed here by a rectangular cross section of pipe 2 or 3 in its region between its outer end and shoulder 22 or 23.

Figure 2:
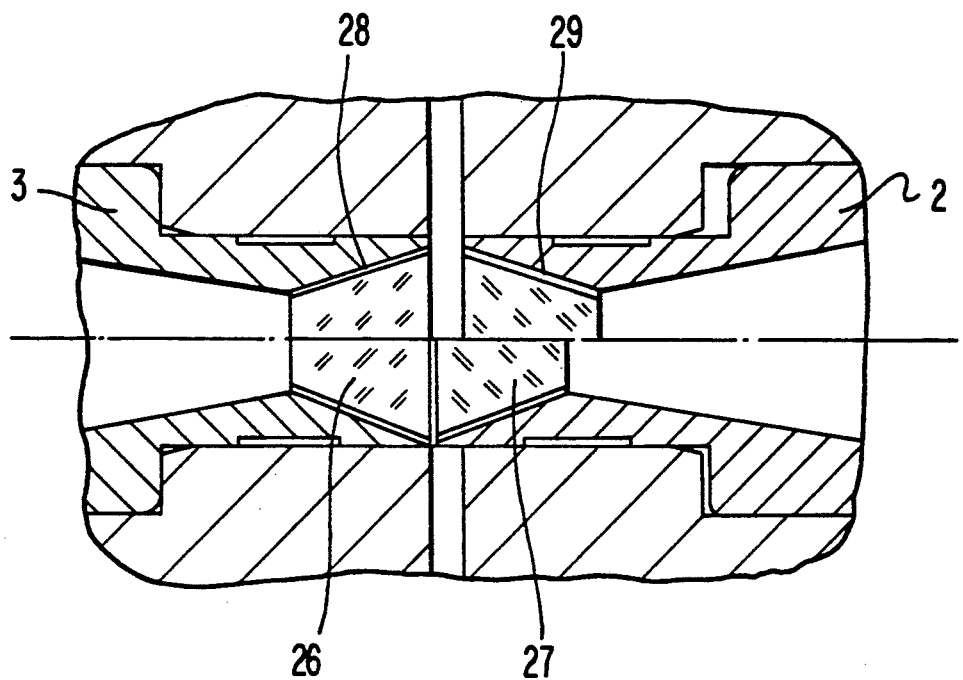
FIG. 2 shows a measuring cell that is constructed in principle in the same manner, but has windows exhibiting a conical shell. As a consequence of the conical design of the windows, they are in a position to absorb especially high pressures.

FIG. 2 shows a measuring cell constructed in the same manner in principle and in which only windows 26 and 27 are designed conically and sit in a corresponding cone of pipe 2 or 3. Windows 26 and 27 are attached with respect to the affected cone in pipes 2 and 3 by means of the adhesive layer 28 or 29. Moreover, the measuring cell according to FIG. 2 is constructed from the same components as the measuring cell according to FIG. 1 so that the identical reference numerals can be used.

It should also be pointed out that it suffices if only one pipe with window is given the axial mobility, provided the uniform flow of medium through gap 7 or 8 is not disturbed.

I claim:

1. Measuring cell for the spectral analysis of flowing media, in particular plastic melts, in which cell the medium to be analyzed flows between two opposing windows (4, 5) made of a radiation transparent material and is penetrated by radiation, where at least one window (4, 5) is held in a pipe (2, 3), which can be moved by axial motion in the direction of the second window (5, 4) or away from said window in a bore (15) of the measuring cell body (1) with said measuring cell body being sealed, where the width of the gap (7, 8) between the windows (4, 5) and thus the layer thickness of the medium through which the radiation is to travel is variable, wherein in the region of the seal with the stepless cylindrical outer surface the pipe (2, 3) abuts directly the wall of the bore (15) and in this region exhibits oversize in the disassembled state relative to the bore (15), wherein the wall thickness of the pipe (2, 3) is small with respect to the outer diameter of the pipe (2, 3) at least in the region of the seal and wherein a layer of adhesive (24, 25) is inserted in a ring slot between the interior of the pipe (2, 3) and the shell of the window (4, 5).

2. Measuring cell, as claimed in claim 1, wherein the region of the seal extends as far as the end of the bore (15) of the measuring cell body (1), said end facing the medium.

3. Measuring cell, as claimed in claim 1 or 2, wherein the adhesive layer (24, 25; 28, 29) is made of a material that is elastic as compared to the material of the window and pipe.

4. Measuring cell, as claimed in claim 1, wherein the shell of the window (4, 5) is designed in the direction of the medium conically with the increase in diameter and the pipe (2, 3) exhibits a corresponding inner cone.

5. Measuring cell, as claimed in any of claim 1, wherein the window surface facing the medium does not project in front of the face (18, 19) of the pipe (2, 3) and lies substantially in one plane with this face (18, 19).

6. Measuring cell, as claimed in claim 1, wherein the outer surface of the pipe (2, 3) is made of wear resistant material at least in the region of the pipe's seal.

7. Measuring cell, as claimed in claim 1, wherein the wall of the bore (15) is made of wear resistant material at least in the region of the seal.

8. Measuring cell, as claimed in claim 1, wherein the pipe (2, 3) is provided with an anti-rotation element in a region facing away from the window (4, 5).

* * * * *